United States Patent [19]

Berger et al.

[11] Patent Number: 4,534,361
[45] Date of Patent: Aug. 13, 1985

[54] METHOD AND APPARATUS FOR MEASURING BLOOD PRESSURE BY INSTANTANEOUS COMPARISON OF MULTIPLE FREQUENCY-RANGE COMPONENTS OF KOROTKOFF NOISE

[75] Inventors: Klaus Berger; Karl-Heinz Affeldt; Lutz Böttcher, all of Berlin, Fed. Rep. of Germany

[73] Assignee: Robert Bosch GmbH, Stuttgart, Fed. Rep. of Germany

[21] Appl. No.: 437,689

[22] Filed: Oct. 29, 1982

[30] Foreign Application Priority Data

Nov. 2, 1981 [DE] Fed. Rep. of Germany ....... 3143372

[51] Int. Cl.³ .............................................. A61B 5/02
[52] U.S. Cl. ..................................................... 128/680
[58] Field of Search ................................ 128/680-683

[56] References Cited

U.S. PATENT DOCUMENTS

| 3,308,811 | 3/1967 | Gillette et al. | 128/680 |
| 3,633,568 | 9/1969 | Hobel | 128/682 |
| 3,814,083 | 6/1974 | Fletcher et al. | 128/683 |
| 4,026,277 | 5/1977 | Toda et al. | 128/680 |
| 4,112,929 | 9/1978 | Affeldt et al. | 128/680 |

FOREIGN PATENT DOCUMENTS

| 2945126 | 6/1981 | Fed. Rep. of Germany . | |
| 0596221 | 3/1978 | U.S.S.R. | 128/680 |

OTHER PUBLICATIONS

Golden, D. et al. "Development of a Korotkoff Sound Processor for Automatic Identification of Auscultatory Events-part 1: Specification of Preprocessing BP Filters", IEEE Trans. on Biomed. Engrg., vol. BME-21, No. 2, pp. 114-118, Mar. 1974.
Wolthius, R. et al., "Development of Korotkoff Sound Processor for Automatic Identification of Auscultatory Events part 2: *Decision Logic Specifications and Operational Verification*", *IEEE Trans. on Biomed. Engrg., vol. BME-21, No. 2, pp. 119-124, Mar. 1974.*
Schulze, A. et al., "A System for the Automatic Measurement and Digital Display of Systolic & Distolic BPs", Southwestern IEEE Conference Records, Apr. 1968, pp. 17F1-17F5.
Graham, M., "Series I Made Medical Transducers, UP's Monitor EKG and BP", Electronic Design 19, Sep. 13, 1976.

*Primary Examiner*—Kyle L. Howell
*Assistant Examiner*—Francis J. Jaworski
*Attorney, Agent, or Firm*—Frishauf, Holtz, Goodman & Woodward

[57] ABSTRACT

To improve the accuracy of blood pressure measurement by utilizing the Korotkoff noises, the frequency spectrum of the Korotkoff noises is analyzed, either by a plurality of filters (16, 17, 18; FIG. 1) or by a Fast Fourier Transform (FFT) system (54, 55; FIG. 2). If a plurality of filters are used (FIG. 1), which may be analog or digital, then the output amplitudes are rectified (19, 20, 21) and quotients are formed. If the quotients have a predetermined relationship, as determined by a discriminator (27, 28), a control logic provides output signals to a manometer (31) to indicate, respectively, systolic and diastolic blood pressure. For Fast Fourier Transform, a microprocessor can be used which, simultaneously, can provide clock sources to digitize output from the microphone coupled to the cuff of the blood pressure measuring instrument.

13 Claims, 2 Drawing Figures

METHOD AND APPARATUS FOR MEASURING BLOOD PRESSURE BY INSTANTANEOUS COMPARISON OF MULTIPLE FREQUENCY-RANGE COMPONENTS OF KOROTKOFF NOISE

REFERENCE TO RELATED PATENT

German Pat. No. 29 45 126, WELTERSBACH.

The present invention relates to a method and apparatus to electronically determine blood pressure, and more particularly to sense and evaluate the Korotkoff noise, and obtain an evaluation therefrom, so that the systolic and the diastolic blood pressure cap be determined.

BACKGROUND OF THE INVENTION

It has previously been proposed to utilize sensing apparatus, such as microphones, which sense the Korotkoff noise, and to so evaluate the obtained outputs from the microphone that blood pressure values can be derived therefrom. Blood pressure apparatus of this type, which operate according to the Riva-Rocci method, have previously been described—see German Pat. No. 29 45 126. This patent discloses that the overall frequency band of the Korotkoff noises are sensed, a small frequency band is filtered therefrom, and the associated amplitudes are then determined. By use of a switching logic, the Korotkoff noises which first arise, and the Korotkoff noises which last arise, as the pressure in a blood pressure measurement cuff is decreased, are evaluated. Thus, the systolic and the diastolic blood pressures can be determined.

It is possible to eliminate interference and disturbance noises by special circuitry. It has been found, however, that the apparatus is subject to malfunction and disturbance with respect to decrease in amplitude. This may result, for example, from unsuitable positioning of the microphone used to sense the Korotkoff noises, or other inappropriate measurement procedures.

SUMMARY OF THE INVENTION

It is an object to improve blood pressure measuring apparatus in which the Korotkoff noises are sensed, so that the evaluation thereof is made more reliable and the measuring accuracy is improved, and to make the apparatus, and method, essentially independent of the position of the microphone.

Briefly, the Korotkoff noises are analyzed with respect to frequency, and a change in the frequency spectrum is sensed; the change in frequency permits associating cuff pressure levels with frequencies which are representative of systolic and diastolic blood pressure.

In accordance with a feature of the invention, the frequency spectrum is analyzed by a plurality of filters; in accordance with another feature of the invention, a Fast Fourier Transform (FFT) arrangement—known as such—is utilized, and change in the frequency spectrum of the Korotkoff noises is then evaluated.

The method, and the system and apparatus, have the advantage that the blood pressure values are analyzed with respect to frequency spectrum of the Korotkoff noises, and change in the spectrum is determined. This permits better analysis of the Korotkoff noises and increases the measuring accuracy of the blood pressure apparatus. The measuring result obtained by the method and apparatus is not nearly as dependent on the position of the microphone as in the prior art, and spurious signals are effectively suppressed.

In accordance with a particularly desirable feature of the invention, the evaluation of the amplitudes of the Korotkoff noises, within frequency ranges, is additionally effected so that the systolic and diastolic blood pressure values are determined by the respective characteristic change in amplitude relationship. Such an evaluation permits utilization of simple and reliable apparatus.

DETAILED DESCRIPTION

Figure 1:
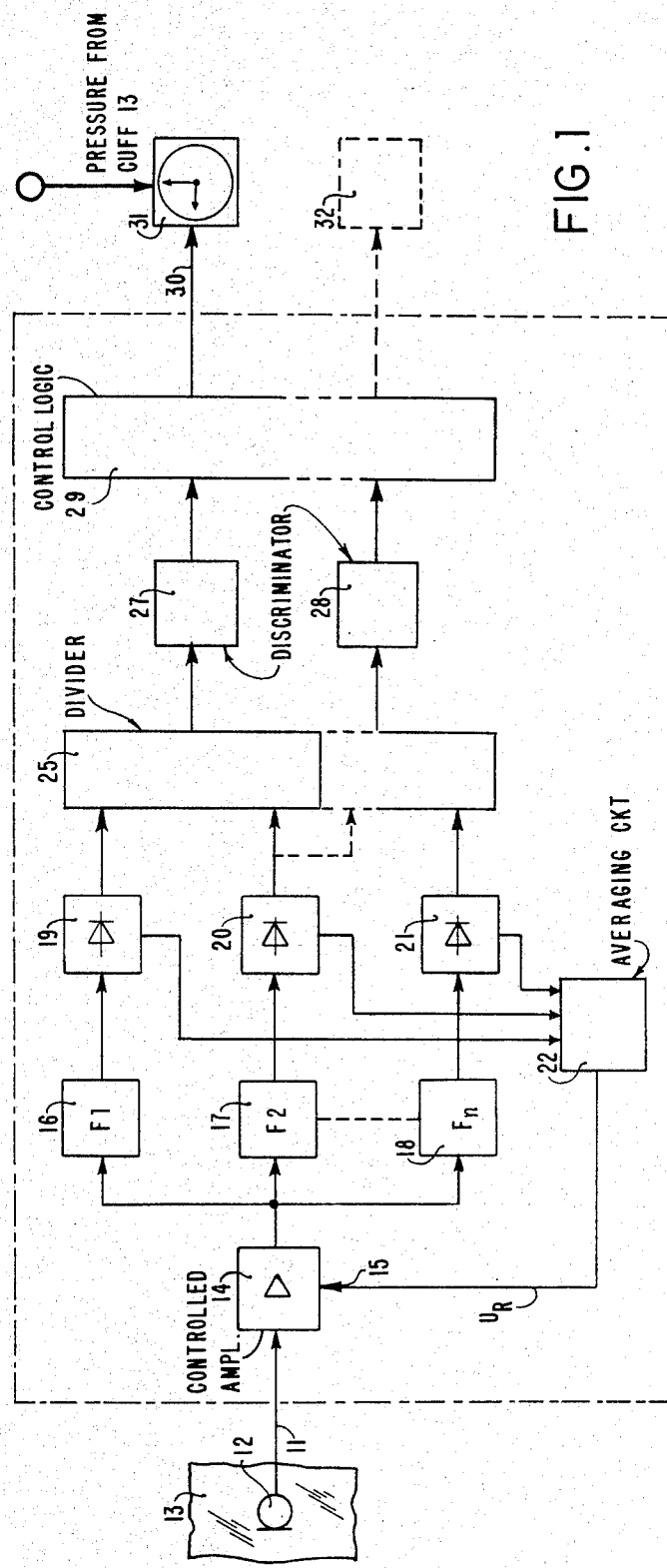
FIG. 1 is a general circuit diagram to evaluate Korotkoff noises by analyzing frequency spectra by filters.

An electronic evaluation apparatus 10 (FIG. 1) is used to evaluate Korotkoff noise which occurs when blood pressure is measured according to the Riva-Rocci method. The apparatus electronically evaluates the noises which are picked by a microphone 12 located, for example, in an inflatable cuff 13. The microphone 12 is connected to the input terminal of the electronic evaluation circuit 10. The input terminal 11 is connected to a controlled amplifier 14, which has a terminal 15 to apply a control voltage $U_R$ thereto. The output of the amplifier 14 is connected to a plurality of band-pass filters 16, 17, also labeled F1, F2, Fn. Only three band-pass filters are shown, which have band-pass characteristics such that adjacent filters, for example filters F1 and F2, are set for adjacent frequency ranges, whereas the last filter Fn is designed to pass a remote frequency band. The frequency band width of the filters is a fraction of the frequency spectrum of the Korotkoff noise: the band of the frequencies of filters F1 to Fn cover the entire noise spectrum of the Korotkoff noises. The broken line between filters 17, 18 indicates that a plurality of filters may be used, more than the three shown, that is, in general n band-pass filters, each designed for an n frequency band-pass.

Each one of the band-pass filters is connected to an associated rectifier 19, 20, 21. The rectifier circuits provide a first d-c output voltage to a network 22 which is connected over a control line 23 with the control input 15 of the controlled amplifier 14. The network 22 averages the output voltages from the respective rectifiers 19-21 to provide a control output voltage to the controlled amplifier 14 to control its amplification to a higher level if the output from the rectifiers 19-21 is low.

Two rectifier circuits, each, for example rectifiers 19, 20, have a further d-c output terminal connected to a divider, that is, a circuit which forms a quotient of the d-c voltages from adjacent rectifiers. A plurality of such quotient-forming circuits 25, 26 . . . are provided. Each one of the quotient-forming circuits 25, 26, is connected to a respective discriminator 27, 28, the output of which is connected to a control logic 29. The output 30 of the control logic 29 is, at the same time, the output from the evaluation circuit 10, and is connected to an indicator 31, for example a two-needle manometer. Rather than using a two-needle manometer, a single-needle manometer may be used which, in association with an optical and/or acoustical signal of an indicator 32 provides a dial-readable output of, respectively, the systolic and the diastolic blood pressure.

Of course, equivalent read-out devices, such as digital liquid crystal or light-emitting diode displays of the respective values can be used.

Operation: The blood pressure measuring cuff 13 is applied, for example to the arm of a person and pressurized above the pressure level of the systolic blood pressure. As well known, the air from the cuff is then slowly permitted to escape. The Korotkoff noises then will occur. The Korotkoff noises which are picked up by the microphone 12 have different frequencies, which are within a Korotkoff noise frequency spectrum. The Korotkoff noise frequency spectrum covers, roughly, the frequencies from between about 20 Hz to 250 Hz.

The electrical signals which are transduced by the microphone 12 are amplified in the controlled amplifier 14, and then separated into frequency bands by the band-pass filters 16, 17, 18 into the ranges F1, F2, Fn. The frequency range F1, for example, includes the frequencies between 18 Hz and 22 Hz. The frequency band F2 includes the range between about 28 Hz and 35 Hz. The last and final frequency band filter may include the range between 180 Hz and 220 Hz. The frequency ranges need not match exactly, one adjacent the other; some gaps may be left, see the ranges between frequencies F1 and F2.

The output voltages from the band-pass filters 16, 17, 18 are rectified in the rectifiers 19, 20, 21. The control voltage $U_R$ is derived from the rectified voltages by the circuit 22. Circuit 22 is provided in order to cause the Korotkoff signal voltages which appear at the output of the controlled amplifier 14 to have a predetermined amplitude even if the blood pressure cuff 13, or the microphone 12, respectively, are improperly positioned.

The d-c voltages derived from the rectifiers are compared, in pairs, in the quotient-forming circuits 25, 26 with respect to each other. For example, at the systolic blood pressure value, the output voltages of the rectifier circuits 19, 20 have a predetermined relationship with respect to each other, which may differ from the predetermined relationship of the output voltages of other rectifier pairs, then the discriminator 27 will determine whether this then predetermined relationship of the Korotkoff noise is present. Discriminator 27 thus will provide a first predetermined signal voltage only if this predetermined relationship at its input is present, that is, if this relationship or quotient of the applied signal voltages is determined by the quotient-forming circuit 25. If this relationship is present, discriminator 27 will provide a first predetermined signal voltage to the control logic 29 which, then, will cause one of the indicators of the two-needle or dual-range indicator 31 to stop at the then pertaining pressure level, as supplied to the manometer by a pressure line, in accordance with well known blood pressure apparatus construction. One of the indicators of the manometer, thus, is stopped, for example mechanically, so that, although the pressure in the cuff continues to drop, the systolic pressure can be read. The systolic blood pressure value thus is stored. Of course, a similar or digital read-out can be provided.

At the diastolic blood pressure, the corresponding Korotkoff noises will result in output voltages of two other rectifier circuit pairs which have a predetermined relationship to each other. This relationship is sensed in one of the other quotient-forming networks, for example the network 26, and applied to the discriminator 28.

The discriminator 28 will respond when these other frequencies have the predetermined relationship, and, if the response is positive, provide an output voltage to the control logic 29 of a predetermined control level, which arrests the second indicator or needle of the dual-needle manometer 31, or otherwise provides an output indication, for example by providing an audible or visual output to indicator 32 altering an operator to read the manometer 31 at that point.

The criterion for the systolic or the diastolic blood pressure, as characterized by the Korotkoff noises, can encompass more than two frequency ranges. If the apparatus is so constructed, then the control logic 29 may include a further logic network, for example formed of AND-gates, which detects the simultaneous occurrence of signal voltages from the outputs of more than one discriminator like the discriminators 27, 28.

The evaluation of the Korotkoff noises is not limited to the audible portion of the noise frequency. Some of the Korotkoff noises are in the infra-audible range, and the frequency spectrum of the Korotkoff noises may have inaudible characteristics, for example low minima, the frequencies of which shift particularly when the diastolic blood pressure value is reached. Thus, evaluation of specific characteristic frequencies and their change provides for unambiguous output.

If only a single-needle or single-indicator manometer is used, or a digital indicator is provided which does not have a memory, then the two signal voltages cause, for example, connection of a first and a second optical and/or acoustical signal which alerts the operator of the blood pressure measurement device to note the indicated pressure values for the systolic and diastolic blood pressure when the signals occur.

The filters F1, F2 . . . Fn may be analog or digital band-pass filters. A microcomputer circuit, of well known arrangement, then causes switch-over of the filters, and frequency analysis by digital control. Such circuits are well known, and a specific circuit arrangement to show frequency analysis by digital filters, thus, is not needed.

The number of the frequency ranges F1, F2 . . . Fn, and hence the number of the filters required, will depend on the desired accuracy of evaluation. This accuracy is increased with the number of filters, and, as the number of filters is increased, consequently, particular physiological characteristics can then be sensed.

If the frequency ranges become high, then the cost of the filters, whether of analog or digital type, may become excessive and, then, it is desirable to utilize the method which includes Fast Fourier Transformation (FFT). This reduces the circuit component requirements, as is illustrated in FIG. 2.

Figure 2:
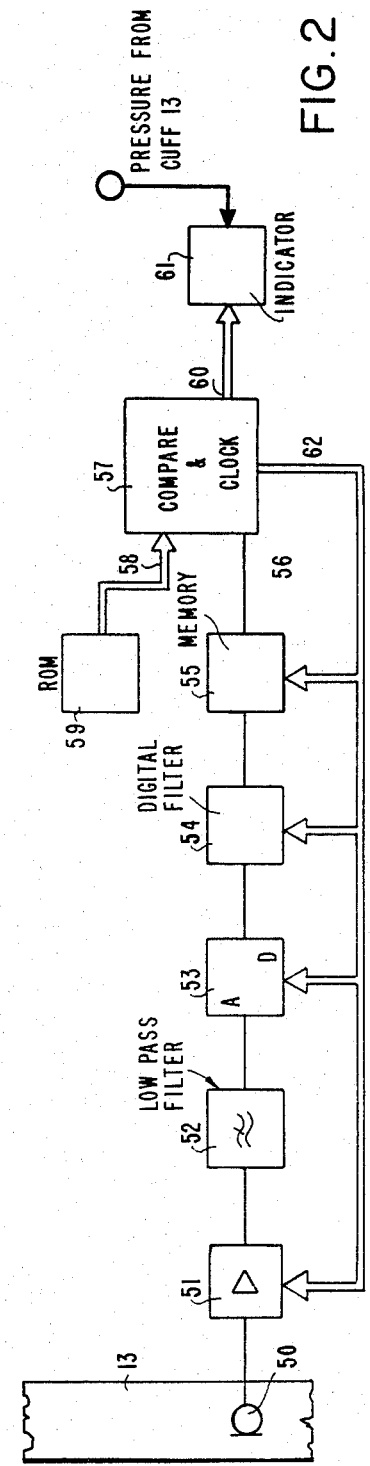
FIG. 2 is a circuit diagram to analyze Korotkoff noises utilizing Fast Fourier Transform for frequency analysis.

Embodiment of FIG. 2: A blood pressure cuff similar to cuff 13 has a microphone 50 connected to a controlled amplifier 51, similar to amplifier 14. A low-pass filter 52 is connected to the output of the amplifier 51. The filter 52 has the characteristic that it eliminates frequencies which, upon a subsequent conversion to digital form in an analog/digital (A/D) converter 53, might approach the digitizing frequencies, so that erroneous inputs are excluded. A digital filter 54 is connected to the A/D converter which, in turn, is connected to a memory 55 which has its output connected to one input of a comparison and clock circuit 57 which may be part of a microcomputer or microprocessor. A comparison or fixed value memory 59, preferably an ROM circuit, is provided, connected to the microprocessor 57. The microprocessor 57 has an output 60 which provides output signals to control the manometer pressure indicator 61.

Microprocessor 57 additionally has a control connection 62 which controls the controllable amplifier 51, the digital filter 54, and the electronic memory 55. The components within the microprocessor 57 which are used in the present invention, essentially, include comparison function and a clock source.

Operation, circuit of FIG. 2: The microphone 50 transduces the Korotkoff noises into alternating voltages which are amplified in the controlled amplifier 51 and are then connected to the low-pass filter 52. Low-pass filter 52 prevents connection of higher frequencies, which may be close to the clock frequency of the A/D converter 53 and which may lead to ambiguities in the digital signal path. The limit frequency of the low-pass filter 52 is designed to be above the highest frequency to be expected within the frequency spectrum of the Korotkoff noises.

The output voltage of the filter 52 is converted into a corresponding digital value in the A/D converter 53. The digital filter 54, controlled by the microprocessor 57, subdivides the Korotkoff noises into spectral components. The entire frequency spectrum or, rather, that frequency spectrum which is necessary for blood pressure measurement, and which contains the important and characteristic portions of the Korotkoff noises, is stored within the memory 55 and compared by the comparator circuit within the microprocessor 57 with fixed frequency values stored in the ROM 59. Systolic and diastolic blood pressure, thus, can be checked based on the amplitude relationship of Korotkoff noises within specific spectral frequency ranges, as well as with respect to change within the spectral frequency ranges and change of amplitude relationships in the respectively changed frequencies within the frequency spectrum of the corresponding noises. The output from output terminal 60 of the microprocessor is connected to an indicator 61, which may be similar to the indicators 31, 32, FIG. 1, and, additionally, can be used to control the sequencing and operation of the respective circuit elements 51, 54, 55 via line 62, by providing the appropriate clock signals and control signals thereto, in order to associate specific frequency ranges with values then to be stored at specific addresses. This control function, to be obtained from a microprocessor, is well known and can be in accordance with any desired arrangement suitable for use with the particular microprocessor then being employed.

Various changes and modifications may be made, and features described in connection with any one of the embodiments may be used with any of the others, within the scope of the inventive concept.

A suitable unit for element 57 (FIG. 2) is: Intel 8085 A.

We claim:

1. Method of blood pressure measurement by sensing the Korotkoff noise and providing an output representative of the characteristic Korotkoff noises occurring at respective systolic and diastolic blood pressure values, comprising the steps of analyzing the Korotkoff noise with respect to frequency to obtain a Korotkoff noise frequency spectrum and comparing the noise amplitudes of the Korotkoff noise in different frequency ranges with each other;

sensing change in the Korotkoff noise frequency spectrum by sensing characteristic changes in the amplitude relationship of compared frequency ranges, characteristic, respectively, of systolic and diastolic blood pressure values; and providing an output indication when the Korotkoff noise has the respective frequency distribution corresponding, respectively, to the Korotkoff noise at the systolic and diastolic pressure.

2. Method according to claim 1, wherein the step of analyzing the Korotkoff noise with respect to frequency comprises digitizing the Korotkoff noise, and evaluating the noise signals by Fast Fourier Transformation;

and the step of sensing change in the frequency spectrum comprises evaluating the amplitude of the Korotkoff noises as digitized, and as transformed into Fourier series.

3. Method according to claim 1, wherein the step of analyzing the Korotkoff noise with respect to frequency comprises applying signals corresponding to the Korotkoff noise to a plurality of frequency filters having different band-pass characteristics within the Korotkoff noise spectrum;

and forming quotients of the amplitudes of signals within respectively different frequency bands.

4. Method according to claim 3, wherein the step of sensing change in the frequency spectrum comprises comparing the output amplitudes of quotients of the frequencies of the Korotkoff noises derived from the respective filters.

5. Method according to claim 1, wherein the step of sensing change in the frequency spectrum of the Korotkoff noise characteristic comprises comparing the frequency noise characteristic of the respective frequency bands of the Korotkoff noises with a reference level, and determining if respective frequencies have a predetermined relationship with respect to the reference level.

6. Method according to claim 1, wherein the step of sensing change in the frequency spectrum comprises sensing the amplitudes of Korotkoff noises within predetermined frequency ranges;

and comparing the amplitudes of respective frequency ranges with each other, and determining those frequency ranges where the comparison results in a predetermined relationship.

7. Blood pressure measuring apparatus comprising a pressure cuff (13);

a Korotkoff noise pick-up microphone (12);

controlled amplifier means (14) connected to and controlled by the microphone (12);

a plurality of frequency band-pass filters (16, 17, 18), each passing a predetermined band of frequencies (F1, F2 . . . Fn) within the Korotkoff noise spectrum;

quotient-forming means (25, 26) comparing the output amplitude from each two band-pass filters;

discriminator means (27, 28) connected to the quotient-forming means (25, 26) and determining if the quotients of the amplitude of the output of the band-pass filters connected to the quotient-forming means have a predetermined relationship;

and a control logic (29) connected to and controlled by said discriminator means and providing an output in dependence on which one of the discriminator means, connected to which one of the pairs of band-pass filters, provides an output representative of said predetermined relationship.

8. Apparatus according to claim 7, wherein the output from the control logic (29) is connected to a manometer receiving a pressure signal from the cuff (13) and providing, respectively, an output indication of the systolic and diastolic pressures in dependence on which one of the discriminators (27, 28) indicates the presence of said predetermined relationship.

9. Apparatus according to claim 7, wherein the amplifier (14) is a controlled amplifier having its amplification level controlled by a control voltage ($U_R$);

a plurality of rectifiers (19, 20, 21) connected to and controlled by said band-pass filters (16, 17, 18);

and connection means (22, 23) connected to and controlled by said rectifiers and providing said control voltage to control the amplification of said controlled amplifier in a direction to compensate for low signal voltages derived from the microphone.

10. Blood pressure measuring apparatus having
an inflatable cuff (13);
a microphone (50) sensing Korotkoff noises;
a controlled amplifier(51) connected to receive analog signals from said microphone (50);
an analog/digital converter (53) connected to digitize the output signals from said amplifier;
a digital filter (54) receiving and separating into spectral components the digitized amplified signals;
an electronic memory (55) for storing said digitized signals;
a memory means (59) adapted for fixed storage of predetermined Korotkoff noise spectral component comparison or reference values;
comparator means (57) comparing the ratios of the amplitude levels of the spectral components stored in said electronic memory (55) with predetermined values stored in the fixed storage memory means (59), and providing an output indication when the Korotkoff noise has the respective frequency distribution corresponding, respectively, to the Korotkoff noise at the systolic and diastolic pressure.

11. Apparatus according to claim 10, wherein said comparator means comprises part of a microprocessor;
said microprocessor additionally including a clock source which is connected to and controls the analog/digital converter (53), the digital filter (54) and the memory (55).

12. Apparatus according to claim 10, further including a low-pass filter (53) interposed between the controlled amplifier (51) and the analog/digital converter (53);
a clock source (57) controlling the digitizing of the amplified signals from the microphone (50) as amplified in the amplifier (51), the filter (52) having a cut-off frequency above the maximum frequency of the Korotkoff noises, but below that of the clock source, to prevent interference between the repetition rate of the clock source and the digitized Korotkoff noises.

13. Apparatus according to claim 10, wherein the digital filter (54) and the memory (55) comprise a Fast Fourier Transform system.

* * * * *